United States Patent [19]
Bucalo

[11] 3,941,136
[45] Mar. 2, 1976

[54] METHOD FOR ARTIFICIALLY INDUCING URINATION, DEFECATION, OR SEXUAL EXCITATION

[75] Inventor: Louis Bucalo, Holbrook, N.Y.

[73] Assignee: Neuronyx Corporation, Holbrook, N.Y.

[22] Filed: Nov. 21, 1973

[21] Appl. No.: 418,106

[52] U.S. Cl. ............................. 128/422; 128/407
[51] Int. Cl.² ........................................... A61N 1/36
[58] Field of Search ........... 128/404, 407, 408, 411, 128/412, 418, 419 E, 419 R, 419 S, 421, 422, 423

[56] References Cited
UNITED STATES PATENTS

| | | | |
|---|---|---|---|
| 335,638 | 2/1886 | Sherwood | 128/404 |
| 2,099,511 | 11/1937 | Caesar | 128/423 |
| 2,932,297 | 4/1960 | Provenza | 128/419 S |
| 3,236,240 | 2/1966 | Bradley | 128/419 E |
| 3,403,684 | 10/1968 | Stiebel et al. | 128/407 |
| 3,640,284 | 2/1972 | DeLangis | 128/422 |
| 3,650,275 | 3/1972 | Mozel | 128/407 |

FOREIGN PATENTS OR APPLICATIONS

| | | | |
|---|---|---|---|
| 1,318,045 | 1/1963 | France | 128/422 |
| 1,145,749 | 3/1969 | United Kingdom | 128/407 |

*Primary Examiner*—William E. Kamm
*Attorney, Agent, or Firm*—Steinberg & Blake

[57] ABSTRACT

A method for artificially inducing urination, defecation, or sexual excitation in human beings or animals. By way of a suitable generator, supplied with power either from a battery or from a wall outlet, electrical pulses are created with a given voltage, frequency, and duration. These electrical pulses are applied at least to the region of the crotch and preferably both to the region of the crotch and to the sacral area beside the spine. For penile or clitoral erection the voltage does not exceed 20 V, while the frequency of the pulses can be 100–200 cycles per second, and the duration of each pulse may be on the order of 200 microseconds, with the generator generating a square wave. During operation it is possible to reduce the initial voltage from a range of 20 V. to a range of 10 V. which is adequate to maintain an erection once achieved.

15 Claims, 8 Drawing Figures

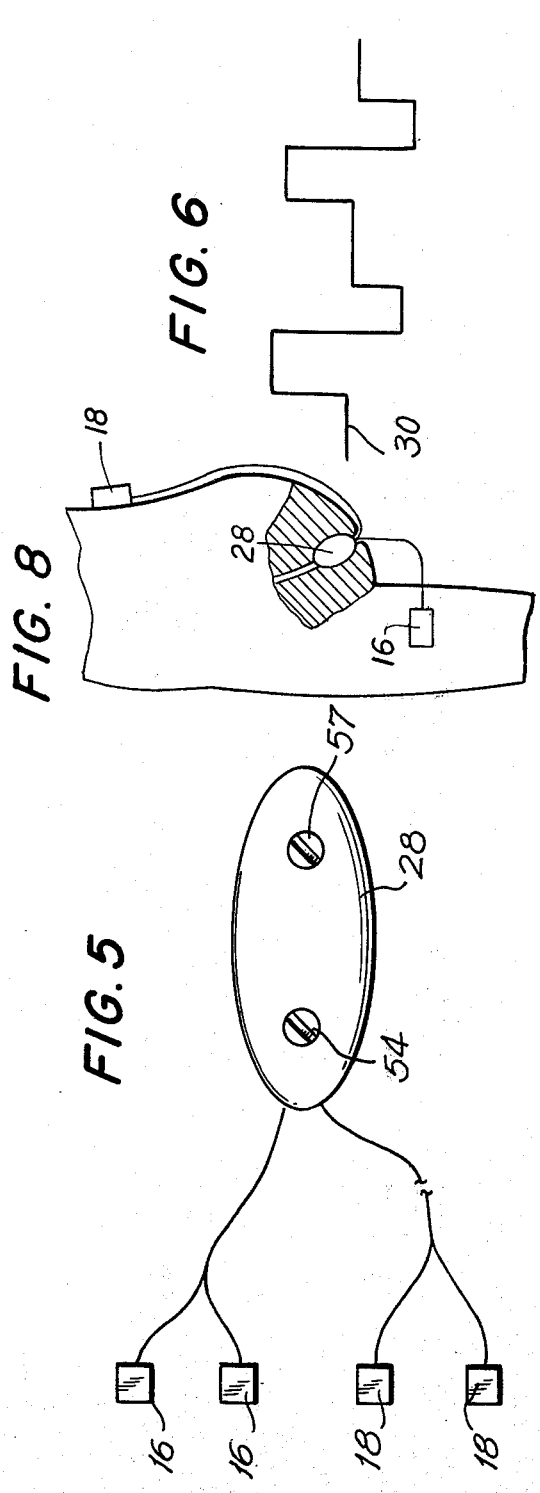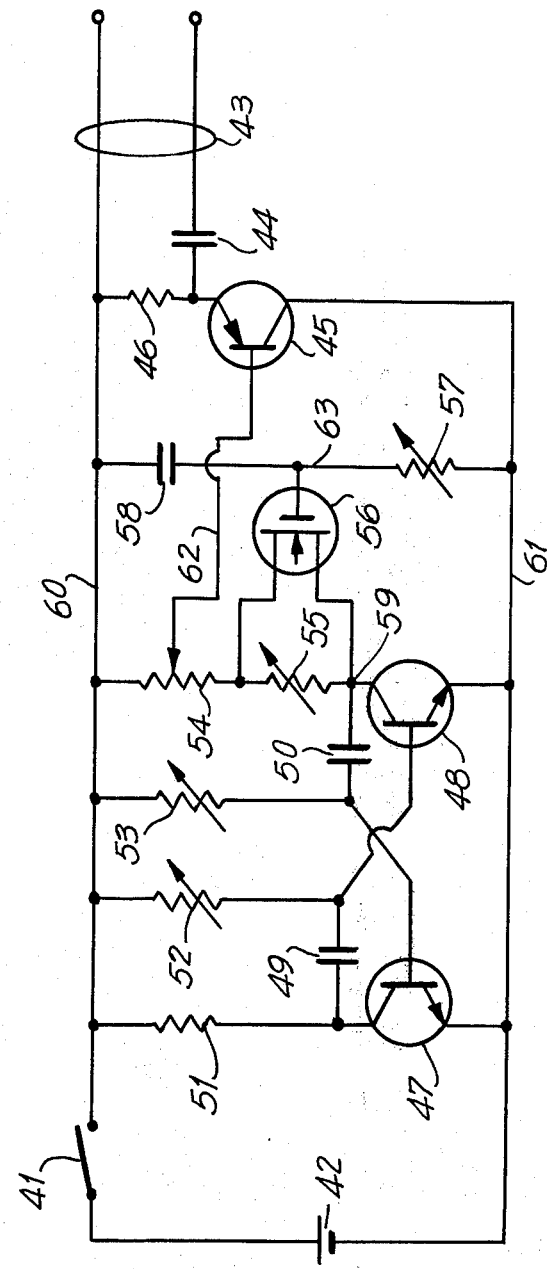

METHOD FOR ARTIFICIALLY INDUCING URINATION, DEFECATION, OR SEXUAL EXCITATION

BACKGROUND OF THE INVENTION

The present invention relates to methods for promoting urination, defecation or sexual excitation in humans or animals.

As is well known, participants in sexual intercourse may encounter difficulties either in achieving an erection or in maintaining an erection once achieved.

While many attempts have already been made to solve this problem, up to the present time a satisfactory solution has not been found. Thus, proposals have already been made according to which mechanical and electrical structures have been used, or surgical procedures have been resorted to, and in addition attempts have been made to introduce into the body, either orally or parenterally, certain substances which are intended to alleviate the problem. However, none of these previous attempts have proved to be desirable or satisfactory in most cases.

Also, it is known that problems are frequently encountered in connection with urination and defecation. For example, paraplegics often require treatment in order to be able to carry out urination, and quite often extremely severe procedures are resorted to such as surgical procedures and implanting of artifical bodies with resultant infection which is almost impossible to avoid unless massive doses of antibiotics are consumed over a long period of time.

In connection with geriatrics, one of the problems most frequently encountered with aging individuals is constipation. Up to the present time no truly satisfactory solution to this problem has been achieved.

SUMMARY OF THE INVENTION

Accordingly it is a primary object of the present invention to provide a method capable of solving the above problems.

In particular, it is an object of the present invention to provide a method which can conveniently be used in order to achieve a desired erection which can be maintained for a considerable period of time without any particular inconvenience or pain.

It is also an object of the present invention to provide a method of the above type which can be used without interfering in any way with normal sexual intercourse.

Furthermore, it is an object of the present invention to provide a method of the above type which can be used for artifically inducing urination and/or defecation.

In particular, it is an object of the invention to provide a method capable of artificially inducing urination and/or defecation without requiring any systemic administration of drugs or other medication, with the problem of side effects resulting therefrom, and also without requiring any surgical procedures.

Also it is an object of the present invention to provide a method of the above type which will have absolutely no harmful side effects.

In addition, it is an object of the present invention to provide a method of the above type which is inexpensive.

In accordance with the invention electrical pulses are created and applied at least to the region of the crotch, although it is preferred to apply the electrical pulses simultaneously to the region of the crotch and sacral area beside the spinal column. The electrical pulses have a voltage which creates no feeling whatsoever or painful electrical shock, and the manner in which the electrical pulses are applied is such that there is no interference whatsoever with activities during sexual intercourse.

BRIEF DESCRIPTION OF DRAWINGS

The invention is illustrated by way of example in the accompanying drawings which form part of this application and in which:

FIG. 5 shows yet another embodiment of a method according to the invention;

FIG. 6 illustrates a wave form generated with structure used in the method of the invention;

FIG. 7 is a wiring diagram of one possible electronic system for achieving the desired controls; and FIG. 8 schematically illustrates the manner in which a generator as shown in FIG. 5 may be situated in the rectum.

DESCRIPTION OF PREFERRED EMBODIMENTS

Figure 1:
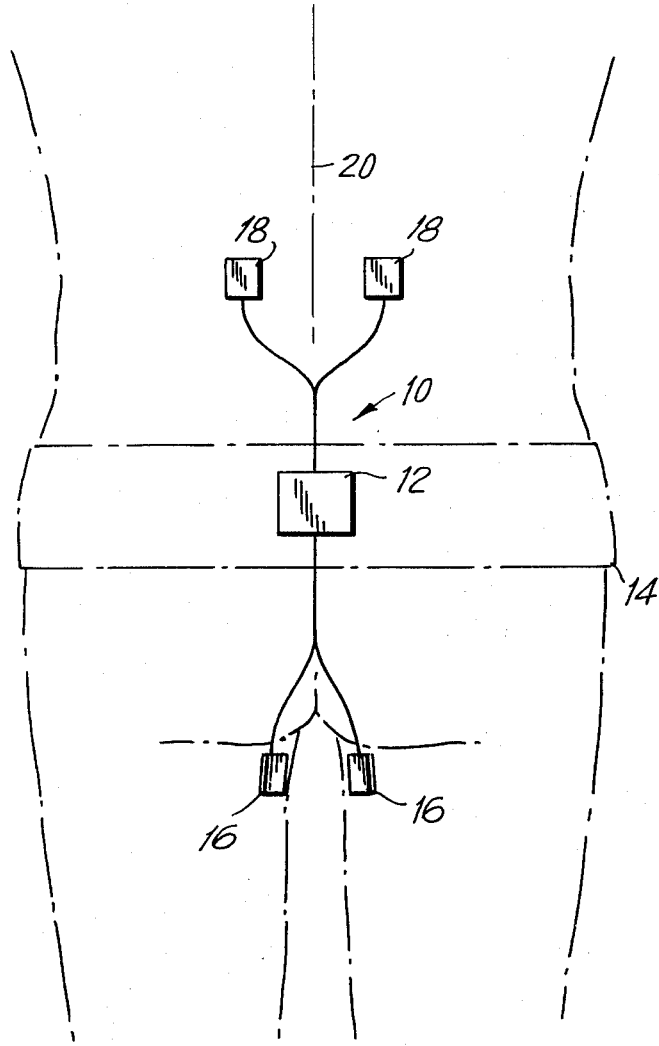
FIG. 1 shows one possible embodiment of a method according to the invention as applied to a human being indicated in phantom lines in FIG. 1 together with an optional strap for holding part of the device on the body, this strap also being indicated in phantom lines.

Referring first to FIG. 1, there is indicated therein a method according to the invention as applied to a human being. However it is to be understood that the method is very valuable for use with all mammals — in connection with breeding with impotent male animals or female animals when they are not in heat, for example. The device 10 includes a generating means 12 capable of generating electrical pulses. This generating means 12 houses its own power supply in the form of one or more batteries, and it is capable of generating electrical pulses having voltages which, for promoting penile or clitoral erection, are no greater than 20 volts at a frequency of 100–200 cycles per second, with each pulse having a duration on the order of 200 microseconds. The generating means 12 generates a substantially square wave form and will have an electrical circuit and electrical components well known in the art for creating pulses having the above characteristics. In the example illustrated in FIG. 1, the generating means 12 is situated at the back of the operator at the region of the coccyx, just above the buttocks and below the sacral area. If desired the generating means 12, which is situated in a suitable housing, can be releasably held in position by way of a strap 14 which is schematically indicated. In practice strap 14 may be an athletic supporter or a hernia belt type of support.

In the example illustrated in FIG. 1 conductors respectively extend from the generating means 12 and terminate in a pair of lower electrodes 16 and upper electrodes 18. The electrodes 16 and 18 may be held in position by the use of any suitable adhesive or by placing adhesive tape over these electrodes to hold them in contact with the exterior body surface. Electrode jelly (NaCl in a jelly base) may be placed between the electrodes and the skin, as known with electrocardiographic electrodes. The pair of electrodes 16 at the region of the crotch may be positive electrodes in which case the electrodes 18 will be negative electrodes while it is also possible to provide positive electrodes 18 and negative electrodes 16. The electrodes 18 are located at the sacral area on opposite sides of the spine 20 which is schematically indicated. Thus, as may be seen from FIG. 1, the electrodes 16 are situated at a region of the crotch which does not form part of an appendage. In other words the electrodes are not situated at the scrotum or penis in case of male animals.

It has been found by experimentation with dogs that it is possible to achieve an erection with a voltage on the order of 20 V, while the erection can be maintained for a period of more than 1 hour with the voltage reduced to the order of 10 V, after the initial voltage of 20 V. Thus, the generator means 12 can be provided with a timer which will automatically reduce the voltage after an initial period, during which a higher voltage is maintained, so that once the erection is achieved the lower voltage may be used for maintaining the erection. A given individual can by way of suitable potentiometers or the like adjust the generator means 12 to determine experimentally the particular voltage required for the particular individual initially in order to achieve the erection and subsequently in order to maintain the erection. Thus, a given individual may require a given voltage of a given frequency and duration in order to achieve the erection initially, and thereafter a different lower voltage with a different frequency or duration may be used to maintain the erection. These different operations will be different for different individuals depending upon physical and psychological characteristics.

As long as the voltage is no greater than 20 V, there is absolutely no painful sensation of shock. For example, during experimentation with dogs, the animals gave no indication of feeling any painful sensation at 10–15 V.

Satisfactory results may also be achieved by providing electrodes only at the region of the crotch, which is of considerable advantage since in this way it becomes possible to render the device practically invisible.

Figure 2:
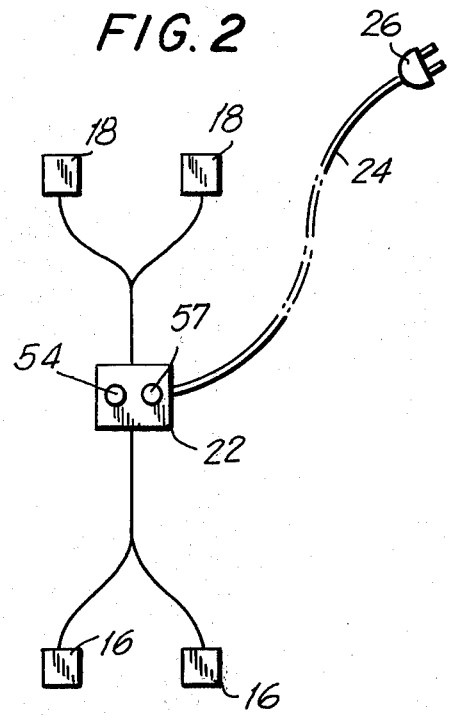
FIG. 2 shows another embodiment of a method according to the invention.

FIG. 2 shows a device according to the invention where a generator means 22 corresponds in all respects to the generator means 12 except that instead of a battery the generator means 22 has a conductive cord 24 provided with a plug 26 which may be inserted in a wall outlet so that in this way a source of power can readily be supplied. Otherwise the electrodes 16 and 18 are identical with that of FIG. 1.

Figure 3:
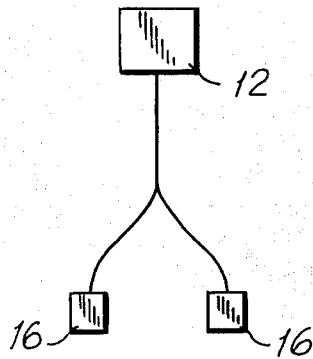
FIGS. 3 and 4 respectively illustrate further embodiments of devices according to the invention.

Referring to FIG. 3, the generator means 12 in this case is connected only with conductors connected electrically to electrodes 16 to be placed at the region of the crotch. With an arrangement as shown in FIG. 3 one of the electrodes 16 will be positive and the other negative.

Figure 4:
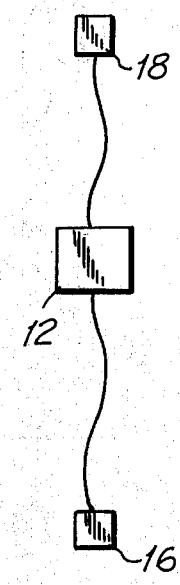

Also, it has been found possible to achieve satisfactory results with an arrangement as shown in FIG. 4 where the generator means 12 is connected through suitable conductors with a single electrode 16 and a single electrode 18. In this case one of these electrodes will be positive and the other negative, and satisfactory results have been achieved irrespective of which electrode is positive and which is negative.

It is also possible to provide an arrangement as shown in FIG. 5 according to which the generator means 28 has an outer housing of the elongated substantially elliptical configuration shown in FIG. 5. The length and cross section of the generator means 28 of FIG. 5 are such that this generator means can conveniently be introduced into the rectum to be maintained therein completely out of sight. Such a location of the generator means 28 in the rectum is schematically illustrated in FIG. 8. Thus by using suitable electronic components any of the generator means described above will be of a relatively small size, and in the case of FIG. 5 the length of the generator means 28 may be no more than 1 or 2 inches while the diameter of the thickest part of the generator means 28 need be no greater than 1 inch. In this case it is possible for the generator means to be connected by way of suitable conductors to a pair of electrodes 16 to be placed at the region of the crotch, as schematically illustrated in FIG. 8. With such a construction the embodiment of FIG. 5 would correspond to that of FIG. 3 according to which the pulses will be applied only to the region of the crotch. However, if desired a longer conductor can also be connected to the generator means 28 and electrically connected with additional electrodes 18 to be applied to the sacral area on opposite sides of the spine. Furthermore, it is possible with a generator having the configuration of the generator means 28 to utilize an arrangement as shown in FIG. 4 according to which one electrode will be located at the sacral area and the other at the region of the crotch. This latter arrangement also is illustrated in FIG. 8.

With any of the generator means of the invention it is preferred to generate initially electrical pulses at voltages on the order of 20 V which after a few minutes can be reduced to a voltage on the order of 10 V. With both of these voltages it is preferred to provide a pulse frequency on the order of 100–200 cycles per second with the duration of each pulse being on the order of 200 microsecond. Also, the generator means of any of the above embodiments will generate a substantially square wave 30 as shown in FIG. 6. It has been found from experience and by actual experimentation that with the generation of such a square wave and with the electrical characteristics referred to above it is possible to achieve an erection in a highly reliable manner while maintaining the erection also in a highly reliable manner for periods even longer than 1 hour.

As is pointed out above, with the method of the invention there is no sensation of painful electrical shock and there are no undesirable side effects. The device is very convenient to use. It can be rendered practically invisible so that there is no psychological deterrent to the activities in connection with sexual intercourse, and even in those embodiments where the device is situated entirely at the exterior of the body, it is located only at the rear where it will not in any way interfere with the sexual intercourse and normally will not be seen from the front.

One possible circuit of the electronic system to be incorporated into the generator 12, 22, or 28 is illustrated in FIG. 7. Thus, FIG. 7 shows one of the many possible circuits capable of providing the desired stimulating current. Stimulation commences when the circuit is energized by closure of switch 41. The circuit provides periodically repeating cycles of stimulation, each cycle consisting of two phases: the pulse phase and the recovery phase. During the pulse phase, a current path is provided from the battery 42, through the switch 41, through the human being or animal under stimulation via electrode connection wires 43, through coupling capacitor 44, and through PNP transistor 45, returning again to the battery 42. Current flow in the pulse conduction path is coincident with and caused by the forward biasing of the base-emitter junction of transistor 45. The recovery phase occurs when transistor 45 is not sufficiently forward biased to conduct. During the recovery phase, current flows from capacitor 44, through the human being or animal under stimulation via electrode wires 43, and through resistor 46 back to capacitor 44. This recovery phase current removes from capacitor 44 the charge deposited on it during the preceding pulse, thus allowing the stimulation to be repeated for an indefinite number of cycles.

Capacitor 44 and resistor 46 are provided to achieve zero average direct current flow through the human being or animal under stimulation, this being a condition which is sometimes found advantageous; it is understood, however, that if capacitor 44 is replaced by direct connection and resistor 46 is omitted, the resulting connection is still effective in achieving stimulation.

The phases of the stimulus cycle are regulated by an astable multivibrator which consists of NPN transistors 47 and 48, capacitors 49 and 50, load resistor 51, recovery phase control resistor 52, pulse duration control resistor 53, and the load impedance presented to transistor 48 by the combination of amplitude control potentiometer 54, amplitude decrement control resistor 55, and the drain source impedance of N-channel enhancement mode field effect transistor 56. Transistors 47 and 48 conduct alternately. Conduction of transistor 48 produces the pulse phase, the duration of which is principally determined by the time constant of resistor 53 and capacitor 50. Conduction of transistor 47 produces the recovery phase, the duration of which is principally determined by the time constant of resistor 52 and capacitor 49.

During conduction of transistor 48, the potential of conductor 59 is reduced from that of conductor 60 to a potential near that of conductor 61. This causes a reduction of potential on conductor 62 which is directly proportional to the setting of potentiometer 54. Due to the emitter-follower action of transistor 45, the output voltage between the electrodes during the pulse phase is nearly equal to the potential reduction on conductor 62. Thus potentiometer 54 controls the magnitude of stimulation.

Furthermore, the insertion of any additional resistance between conductors 62 and 59 must produce a decrease in the amplitude of stimulation. Resistor 55, transistor 56, resistor 57, and capacitor 58 form an automatic means for producing such a decrease a predetermined period of time after the start of stimulation. Immediately after switch 41 is closed, the potential of conductor 63 is that of conductor 60, as the initial charge on capacitor 58 is zero. Current flowing through resistor 57, however, places charge on capacitor 58, reducing the potential on conductor 63 exponentially toward that of conductor 61. As long as the potential difference between conductor 63 and conductor 59 during the pulse phase remains higher than the turn on potential of transistor 56, resistor 55 will be effectively short circuited during the pulse. Once the potential of conductor 63 has dropped to the point where transistor 56 no longer turns on during the pulse phase, the presence of resistor 55 will cause the desired decrease in the amplitude of stimulation. Capacitor 58 and resistor 57 are chosen to provide the desired delay, while resistor 55 is chosen to provide the desired proportion by which the amplitude of stimulation will decrease.

Thus, as is schematically indicated in FIGS. 2 and 5, the housings of the generators may have accessible at their exteriors suitable control knobs or the like for adjusting the potentiometers 54 and 57. In the case of FIG. 5, the control knobs are in the form of rotary discs which are flush with the exterior surface of the housing so that the unit shown in FIG. 5 can be introduced into the rectum without any discomfort.

As has been indicated above, the method of the invention is also useful in connection with artificially inducing urination and/or defecation. Exactly the same structure is used in exactly the manner described above for these purposes. The only difference is that the voltage level is higher than 20 V. Thus it has been found that in a range of over 20 V, it is possible to induce, in a fully artificial manner, urination as well as defecation. While the voltage level is higher than indicated above in connection with penile or clitoral erection, nevertheless the amperage is so low that no unpleasant pain is encountered. Thus, in connection with urination and defecation the invention is useful also with female as well as male mammals. It has been found, most surprisingly, that with the method and device of the invention as described above, utilizing the higher voltage level, a true urination reflex is produced in a fully artificial manner. This result is of great significance since the artifically induced true urination reflex is achieved without any cutting taking place at the body and without the introduction of any artificial components into the body as well as without any systemic administration of drugs or other medications.

In experiments which have been carried out with dogs, after the animal had emptied its bladder, it was possible to achieve with the method of the invention as described above, but with the higher voltage level, a reaction in a male dog where he lifted his leg and went through the urination action. This result was achieved even when the animal was in an uncomfortable position. For example while a dog was maintained lying down, a completely unnatural posture for urination, with the method and device of the invention it was possible to induce artificially a urination which the dog carried out while lying down.

Also, with the above method, at the voltage level of above 20 V, defecation was artificially induced. The defecation was brought about artificially with the same procedures as those used in connection with artificial inducing of urination, and in fact simultaneous urination and defecation is not at all undesired. Thus, it has been found that in a range of over 20 V, for example between 25 and 30 V, the method of the invention was effective in inducing artificial urination and defecation.

What is claimed is:

1. In a method of artificially inducing one of a plurality of body functions, namely urination, defecation and sexual excitement, comprising the steps of applying at least to a region of the crotch which does not form part of an appendage electrical pulses which have for said one body function a given voltage, frequency and duration.

2. In a method as recited in claim 1 for promoting penile or clitoral erection and wherein the voltage is no greater than 20 volts while the frequency is at a range of 100–200 cycles per second, and the duration of each pulse is on the order of 200 microsecond.

3. In a method as recited in claim 2 and including the step of initially providing a voltage on the order of 20 volts until an erection is achieved and then reducing the voltage to the order of 10 volts for maintaining the erection.

4. In a method as recited in claim 1 and wherein the electrical pulses have a substantially square wave form.

5. In a method as recited in claim 1 and including the step of placing a pair of electrodes in engagement with said crotch region with said electrodes respectively being positive and negative electrodes.

6. In a method as recited in claim 1 and including the step of applying the pulses simultaneously at the crotch region and at the sacral area on one side of the spine.

7. In a method as recited in claim 6 and including the step of applying the pulses by way of positive and negative electrodes while situating one of said electrodes at the crotch region and the other at the sacral area.

8. In a method as recited in claim 6 and including the step of applying the pulses by way of a pair of electrodes while situating the latter electrodes at the crotch region and also applying the pulses by way of a second pair of electrodes while situating said second pair of electrodes at the sacral area on opposite sides of the spine, one of the pairs of electrodes being positive and the other pair being negative.

9. In a method as recited in claim 8 and including the step of situating the positive electrodes at the crotch region and the negative electrodes at the sacral area.

10. In a method as recited in claim 8 and including the step of situating the positive electrodes at the sacral area and the negative electrodes at the crotch region.

11. In a method as recited in claim 1 and including the step of situating at the back a generator unit from which the pulses are derived.

12. In a method as recited in claim 11 and including the step of strapping the generator unit onto the back.

13. In a method as recited in claim 11 and including the step of connecting the generator unit to a source of electricity and converting the source into the pulses by way of said generator unit.

14. In a method as recited in claim 11 and including the step of inserting the generator unit into the rectum.

15. In a method as recited in claim 1, for artificially inducing one of the body functions namely urination and defecation, and wherein the voltage is greater than 20 volts while the frequency is at a range of 100–200 cycles per second and the duration of each pulse is on the order of 200 microsecond.

* * * * *